(12) United States Patent
Ahn

(10) Patent No.: US 12,064,610 B2
(45) Date of Patent: Aug. 20, 2024

(54) SKIN TREATMENT DEVICE USING RADIOFREQUENCY AND MEDICATION AND INCLUDING TIGHTENING MEMBER

(71) Applicant: AGNES MEDICAL CO., LTD, Seongnam-si (KR)

(72) Inventor: Gunyoung Ahn, Seongnam-si (KR)

(73) Assignee: AGNES MEDICAL CO., LTD., Seongnam-si (KR)

( * ) Notice: Subject to any disclaimer, the term of this patent is extended or adjusted under 35 U.S.C. 154(b) by 396 days.

(21) Appl. No.: 17/552,969

(22) Filed: Dec. 16, 2021

(65) Prior Publication Data

US 2023/0173194 A1    Jun. 8, 2023

(30) Foreign Application Priority Data

Dec. 2, 2021 (KR) .......................... 10-2021-0170589

(51) Int. Cl.
*A61M 5/42* (2006.01)
*A61M 5/32* (2006.01)
*A61N 1/40* (2006.01)

(52) U.S. Cl.
CPC .......... *A61M 5/422* (2013.01); *A61M 5/3298* (2013.01); *A61M 2205/0216* (2013.01); *A61M 2205/3606* (2013.01); *A61M 2205/3673* (2013.01); *A61N 1/403* (2013.01)

(58) Field of Classification Search
CPC .................. A61M 5/422; A61B 18/14; A61B 2018/00154; A61B 2018/00202; A61B 2018/0047; A61B 2018/143
See application file for complete search history.

(56) References Cited

U.S. PATENT DOCUMENTS

2003/0050602 A1* 3/2003 Pettis ..................... A61M 5/28
604/117
2005/0137531 A1* 6/2005 Prausnitz ............... A61B 5/151
604/173
(Continued)

FOREIGN PATENT DOCUMENTS

| JP | 2018-029892 A | 3/2018 |
| KR | 10-2016-0101472 A | 8/2016 |
| KR | 20-2020-0001727 U | 8/2020 |

OTHER PUBLICATIONS

Korean Office Action for related KR Application No. 10-2021-0170589 mailed Oct. 23, 2023 from Korean Intellectual Property Office.

*Primary Examiner* — Courtney B Fredrickson
(74) *Attorney, Agent, or Firm* — Paratus Law Group, PLLC

(57) ABSTRACT

A skin treatment device using both a radiofrequency and medication and including tightening members, includes a skin expansion module configured to stretch a region of the skin into which first needles are inserted to be tightened, the skin expansion module including a guide body protruding outward from a lower end of a handpiece main body and a pair of tightening members hinge-coupled to hinge shafts provided on a left side and a right side of the guide body to be rotatable, wherein lower ends of the pair of tightening members are spread outward while pressurizing the skin in contact with the skin when the handpiece main body is moved downward.

13 Claims, 11 Drawing Sheets

(56) References Cited

U.S. PATENT DOCUMENTS

| | | | |
|---|---|---|---|
| 2015/0209563 A1* | 7/2015 | Amir | A61M 37/0015 53/473 |
| 2019/0209817 A1* | 7/2019 | Ahn | A61N 1/28 |
| 2023/0029081 A1* | 1/2023 | Van Oorschot | A61B 5/150152 |

* cited by examiner

SKIN TREATMENT DEVICE USING RADIOFREQUENCY AND MEDICATION AND INCLUDING TIGHTENING MEMBER

CROSS-REFERENCE TO PRIOR APPLICATION

This application claims priority to Korean Patent Application No. 10-2021-0170589 (filed on Dec. 2, 2021), which is hereby incorporated by reference in its entirety.

BACKGROUND

The present disclosure relates to a skin treatment device, and particularly, to a skin treatment device using both a radiofrequency and medication, in which heat is generated from a high-frequency current and a drug is injected to improve a treatment effect, and the skin is stretched to be tightened during the insertion of needles so as to facilitate the insertion of the needles, the generation of the heat, and the injection of the drug.

In general, a high-frequency current refers to an alternating current (AC) of 100,000 Hz or more, has a short amplitude, thus causing no electrochemical reaction or electrolysis phenomenon, and causes conversion of vibration current energy into thermal energy only within a predetermined path.

In particular, when a high-frequency current is supplied to human tissue, ionic motions barely occur due to a very short amplitude, and an electrochemical reaction or the electrolysis phenomenon do not occur. When high-frequency electrical energy is supplied to tissue, molecules constituting the tissue are vibrated and rubbed against each other whenever a direction of a current changes, thereby generating biological heat.

In addition, high frequencies do not stimulate sensory nerves and motor nerves unlike other current forms, do not cause irritation or muscular contraction in the human body, and generate heat energy, and the heat energy may enhance functions of cells and increase a blood flow rate.

Therefore, high-frequency treatment devices have been used for various treatment purposes, e.g., skin regeneration, lifting, and suppression of melanin pigment, obesity treatment, skin care, promotion of hair growth, pain relief, and the like.

Recently, skin treatment devices using both high frequencies and medication for continuous skin improvement effects have been introduced. As shown in FIG. 1, such a skin treatment device using a radiofrequency and medication includes a handpiece main body 10, a needle part 30 with a plurality of needles to be inserted into the skin, and a horseshoe-shaped skin expander 20 configured to pressurize the skin to stretch the skin when the needles are inserted into the skin.

In the related art, the horseshoe-shaped skin expander 20 is configured to pressurize the skin to stretch the skin while the needles are inserted into the skin so that the needles may be easily inserted and pain may be relieved.

However, with the horseshoe-shaped skin expander 20, a region of the skin into which the needles are inserted cannot be sufficiently expanded but only swells to a certain degree. Therefore, there is a limit in facilitating the insertion of the needles and relieving pain during the insertion of the needles. Moreover, it is difficult to precisely control a depth of insertion of the needles.

SUMMARY

To address the above problems of the related art, the present disclosure provides a skin treatment device using both a radiofrequency and medication, in which heat is generated from a high-frequency current and a drug is injected to improve a treatment effect and the skin is stretched to be tightened during the insertion of needles so as to facilitate the insertion of the needle, the generation of heat, and the injection of the drug.

According to an aspect of the present disclosure, a skin treatment device using both a radiofrequency and medication includes: a handpiece main body; a needle module including a needle holder installed outside a lower end of the handpiece main body and including a hollow portion, and multiple first needles protruding downward from a lower end of the needle holder, including a hollow portion communicating with the hollow portion of the needle holder, and configured to be inserted into the skin; a high-frequency generator provided in the handpiece main body and electrically connected to the first needles to supply a high-frequency current to the first needles, thereby generating heat; a drug provider provided in the handpiece main body to communicate with the hollow portion of the needle holder and configured to provide a drug to the first needles; and a skin expansion module configured to stretch a region of the skin into which lower ends of the first needles are inserted to be tightened, the skin expansion module including a guide body protruding outward from the lower end of the handpiece main body and a pair of tightening members hinge-coupled to hinge shafts provided on a left side and a right side of the guide body to be rotatable, wherein lower ends of the pair of tightening members are spread outward while pressurizing the skin in contact with the skin when the handpiece main body is moved downward.

Here, an elastic member may be provided in the guide body to elastically support the tightening members and maintain the tightening members to be inclined at a certain angle in an initial state in which an external force is not applied, and the pair of tightening members may be more strongly and elastically supported by the elastic member as the pair of tightening members become spread while in contact with the skin.

The tightening members may each include a skin contact part inclined to be spread outward when a lower end thereof is pressed in contact with the skin, and a rotational coupling part integrally formed with an upper end of the skin contact part and hinge-coupled to the hinge shafts provided on the left and right sides of the guide body to be rotatable about the hinge shafts, wherein support bumps may protrude upward from an upper end of the rotational coupling part to be moved away from the skin contact part with respect to the hinge shafts and may be more strongly and elastically supported on the elastic member as the skin contact parts are spread outward.

The skin treatment device may further include a stopper bump protruding from a position on an upper end of the rotational coupling part of the tightening member, which is spaced outward from the support bump, the stopper bump being configured to be caught by an outer side of the guide body to block further rotation of the skin contact part when lower lines of the pair of skin contact parts are at the same height as a bottom side of the guide body.

The elastic member may be provided as a circular arc shaped leaf spring gradually curved upward toward left and right ends from a central portion supported on an inner bottom surface of the guide body to elastically support the support bumps of the tightening members by the left and right ends of the elastic member, and the left and right ends of the elastic member may be further provided with inwardly curved contact parts corresponding to the support bumps to be in continuous contact with the support bumps regardless of an angle of rotation of the tightening members.

A fixing part having a semicircular groove to be fixed by being fitted onto an outer circumferential surface of a cylindrical spacer of the guide body may be further formed in front of and behind the central portion of the elastic member.

A non-slip member having a strip shape and having a higher coefficient of friction than that of the skin contact part may be further attached to a lower line of the skin contact part of the tightening member.

The skin expansion module may be formed of a thermally conductive metal material and further include a heat transfer member in contact with a cooling unit installed in the handpiece main body to supply a cooling source to the guide body.

A lower side of the guide body may be provided as a flat surface to increase an area of the skin to be cooled.

The cooling unit may include a thermoelement disposed in contact with the heat transfer member and configured to supply a cooling source.

The needle module may further include multiple second needles protruding downward from the lower end of the needle holder and electrically connected to the high-frequency generator to be supplied with a high-frequency current and generate heat, the first needles may be configured to inject a drug in a state in which lower ends thereof reach a reticular hypodermis layer when the first needles are inserted into the skin, and to be supplied with a high-frequency current and generate heat, and the second needles may be shorter than the first needles and configured to be supplied with a high-frequency current and generate heat when lower ends thereof reach a papillary dermis layer when the second needles are inserted into the skin.

The first needles configured to be inserted into the reticular hypodermis layer may be disposed at a midpoint on the needle holder and in the vicinity of the midpoint to be spaced apart from each other, and the second needles configured to be inserted to the papillary dermis layer may be disposed between the first needles around the first needle at the midpoint to increase a density of heat from the high-frequency current to be higher than a density of heat at the reticular hypodermis layer.

A bending prevention base may be fitted onto an outer circumferential surface of each of the first needles longer than the second needles.

The first needles may protrude downward by 1.0 mm from the needle holder, and the second needles may protrude downward by 0.4 mm from the needle holder.

BRIEF DESCRIPTION OF THE DRAWINGS

The above and other objects, features and advantages of the present disclosure will become more apparent to those of ordinary skill in the art by describing exemplary embodiments thereof in detail with reference to the accompanying drawings, in which.

DETAILED DESCRIPTION

Figure 1:
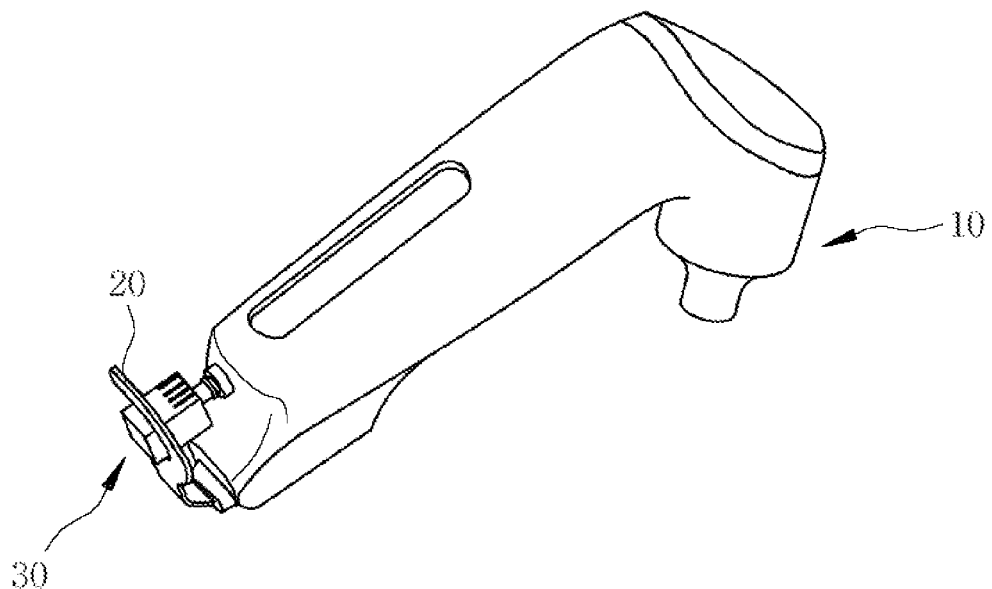
FIG. 1 is a perspective view of a skin treatment device of the related art.

A skin treatment device according to embodiments of the present disclosure will be described in detail with reference to the accompanying drawings. The present disclosure may be embodied in many different forms and implemented in various embodiments. Thus, certain embodiments are illustrated in the drawings and described in detail herein. However, it should be understood that the present disclosure is not limited to particular embodiments and include all modifications, equivalents, and alternatives falling within the idea and scope of the present disclosure. In describing each drawing, similar reference numerals are used for similar elements. In the accompanying drawings, the dimensions of the structures are shown to be larger than actual dimensions thereof for clarity or are shown to be smaller than the actual dimensions to aid in understanding of schematic configurations thereof.

Terms such as first, second, and the like may be used to describe various components, but the components should not be limited by the terms. The terms are only used to distinguish one component from another component. For example, a first component may be referred to as a second component without departing from the scope of the present disclosure, and similarly, a second component may also be referred to as a first component. Unless defined otherwise, all terms used herein, including technical or scientific terms, have the same meaning as commonly understood by those of ordinary skill in the art to which the present disclosure pertains. Terms such as those defined in a commonly used dictionary should be interpreted as having meanings consistent with meanings in the context of related technologies and should not be interpreted as ideal or excessively formal meanings unless explicitly defined herein.

<Embodiments>

Figure 2:
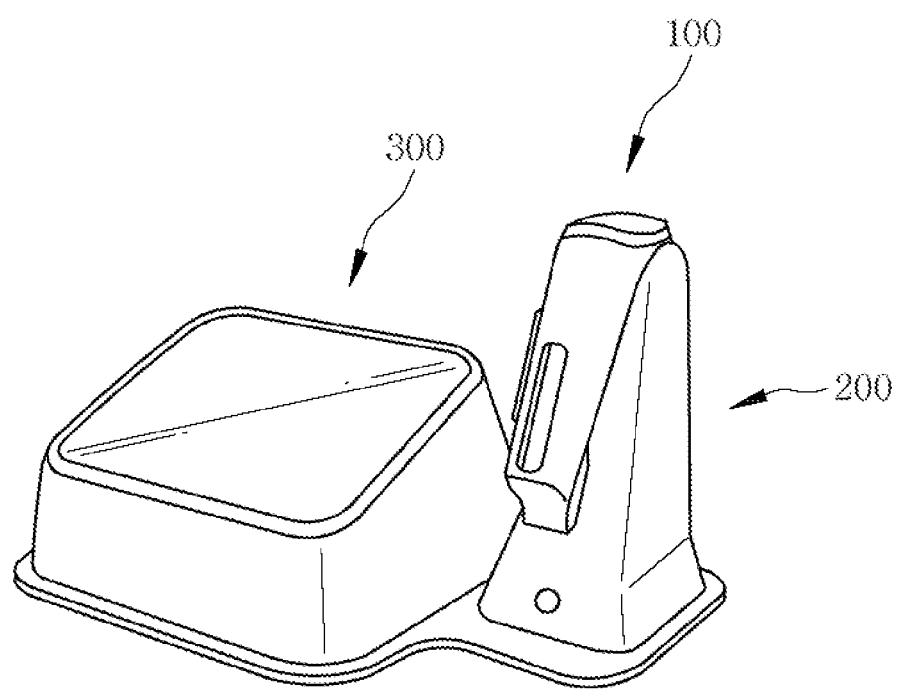
FIG. 2 illustrates a skin treatment system with a skin treatment device according to an embodiment of the present disclosure.
Figure 3:
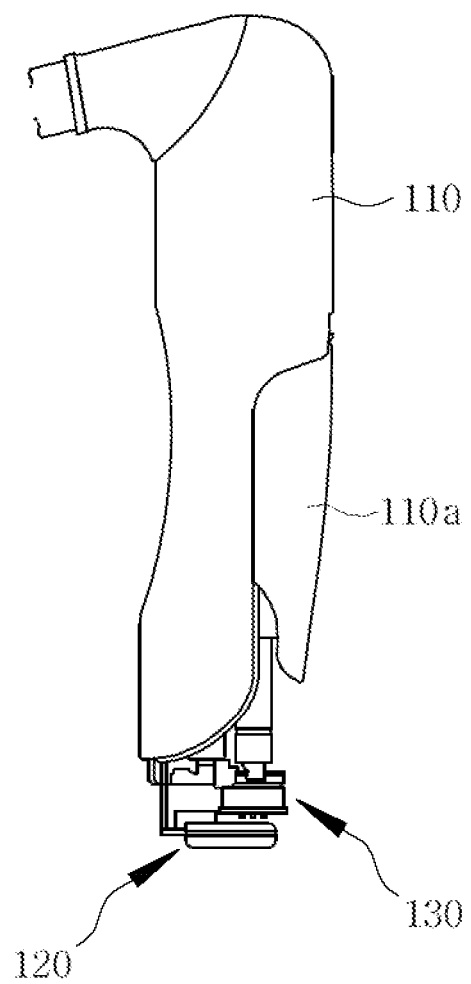
FIG. 3 is a side view of a skin treatment device according to an embodiment of the present disclosure.

FIG. 2 illustrates a skin treatment system with a skin treatment device according to an embodiment of the present disclosure. FIG. 3 is a side view of a skin treatment device according to an embodiment of the present disclosure. FIG.

4 is an exploded perspective view of a skin treatment device according to an embodiment of the present disclosure.

As shown in FIG. 2, in a skin treatment device 100 according to the embodiment of the present disclosure, a treatment device supporter 200 and a treatment device controller 300 form a skin treatment system.

The skin treatment device 100 according to the embodiment of the present disclosure is a core device configured to generate heat from a high-frequency current and inject a drug through insertion of first needles 132a and second needles 132b into the skin of a patient. The treatment device supporter 200 is configured to hold the skin treatment device 100 to be charged or sterilized by a separate device while being held by the treatment device supporter 200 and configured to store components to replace those of the skin treatment device 100. The treatment device controller 300 is a device configured to guide state information of the skin treatment device 100 or allow an operation of the skin treatment device 100 to be set by a user. The treatment device controller 300 may include a touch panel display and be configured to guide various types of information about a power mode, an operation mode, etc. of the skin treatment device 100 and allow a user to change an operation mode or the like to set the treatment device controller 300.

Here, the skin treatment device 100 according to the embodiment of the present disclosure includes a handpiece main body 110, a needle module 130, a high-frequency generator (not shown), a drug provider 140, and a skin expansion module 120 as main components to generate heat from a high-frequency current and inject a drug, thereby enhancing a treatment effect, and stretch a region of the skin into which needles are inserted to be tightened so that the first needles 132a and the second needles 132b may be easily inserted and the generation of heat and the injection of the drug may be smoothly implemented, thereby greatly enhancing the skin treatment effect.

The skin treatment device according to the embodiment of the present disclosure will now be described in more detail with respect to the above-described components.

The handpiece main body 110 is configured in a streamlined shape to allow a user to easily conduct a treatment on a patient's skin while grasping the skin treatment device 100 with a hand and includes a button and a display at a side thereof to control an operation of the skin treatment device 100, e.g., to operate or stop the skin treatment device 100.

A high-frequency generator (not shown) configured to supply a high-frequency current to the first needles 132a and the drug provider 140 configured to supply a drug to the first needles 132a are included in the handpiece main body 110. A syringe installation groove is formed to be recessed in the handpiece main body 110 to detachably install a syringe 141 of the drug provider 140, and a syringe holder may be provided inside the syringe installation groove to press in and support a cylinder part 141a of the syringe 141. The syringe installation groove may be opened or closed by a handpiece cover 110a rotatably installed on the handpiece main body 110. The handpiece cover 110a may be provided as a transparent window to allow a state of a drug in the syringe 141 to be checked with a naked eye.

The high-frequency generator and the drug provider 140 included in the handpiece main body 110 are connected to an external control device via wire or wirelessly to receive a control signal. The handpiece main body 110 may also be provided with various types of sensors to detect state information of the components of the skin treatment device 100 to transmit state information data of the skin treatment device 100 to the treatment device controller 300 or receive a control signal for controlling an operation from the treatment device controller 300.

Figure 9:
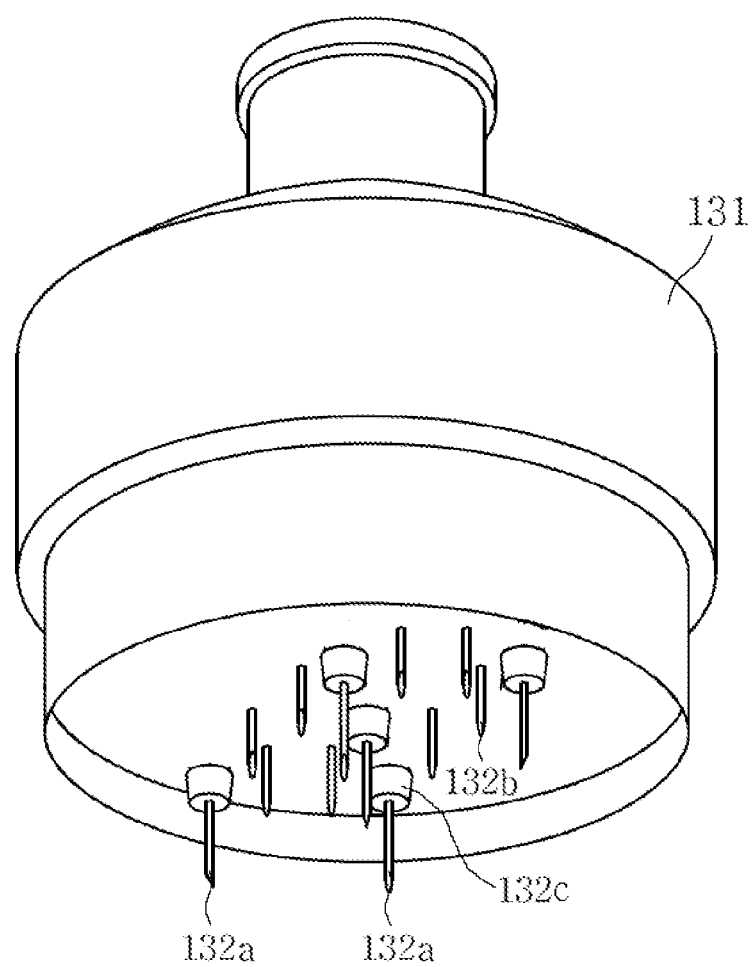
FIG. 9 is a perspective view of a needle module of a skin treatment device according to an embodiment of the present disclosure.

As shown in FIG. 9, the needle module 130 is provided outside a lower end of the handpiece main body 110 and includes a needle holder 131 having a hollow portion and first needles 132a and second needles 132b having different lengths and protruding downward from the lower end of the needle holder 131.

Figure 11:
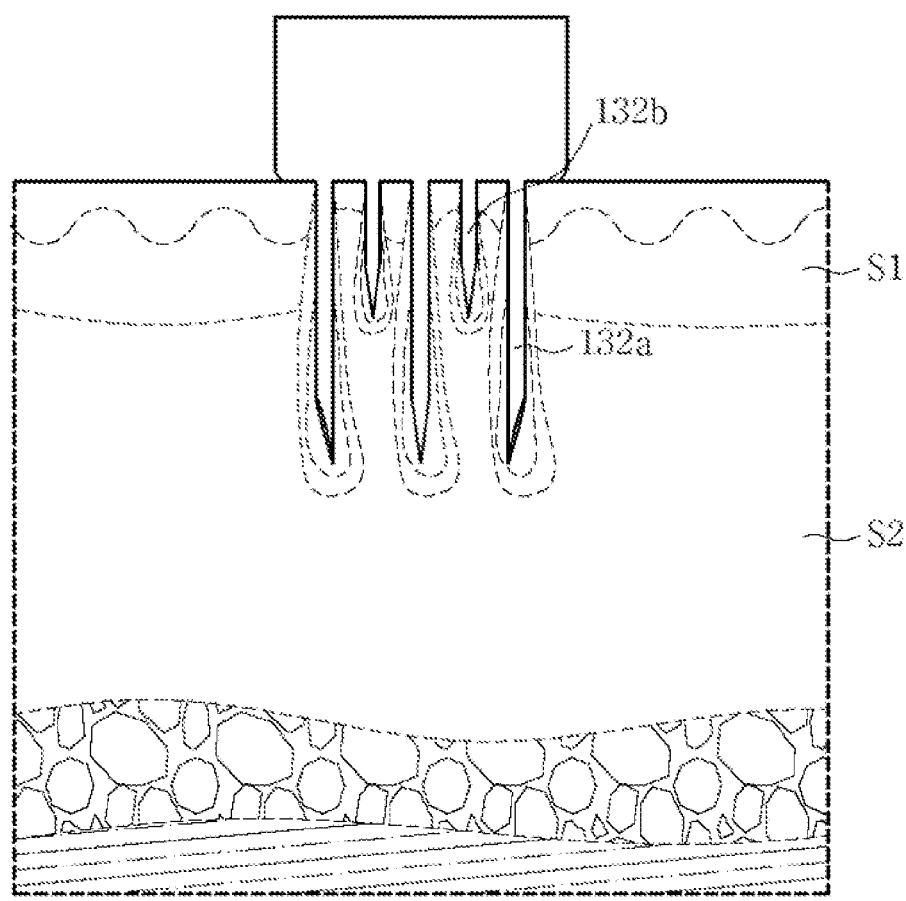
FIGS. 11 and 12 are a series of reference diagrams for describing effects and operations of a first needle and a second needle in a skin treatment device according to an embodiment of the present disclosure.
Figure 12:
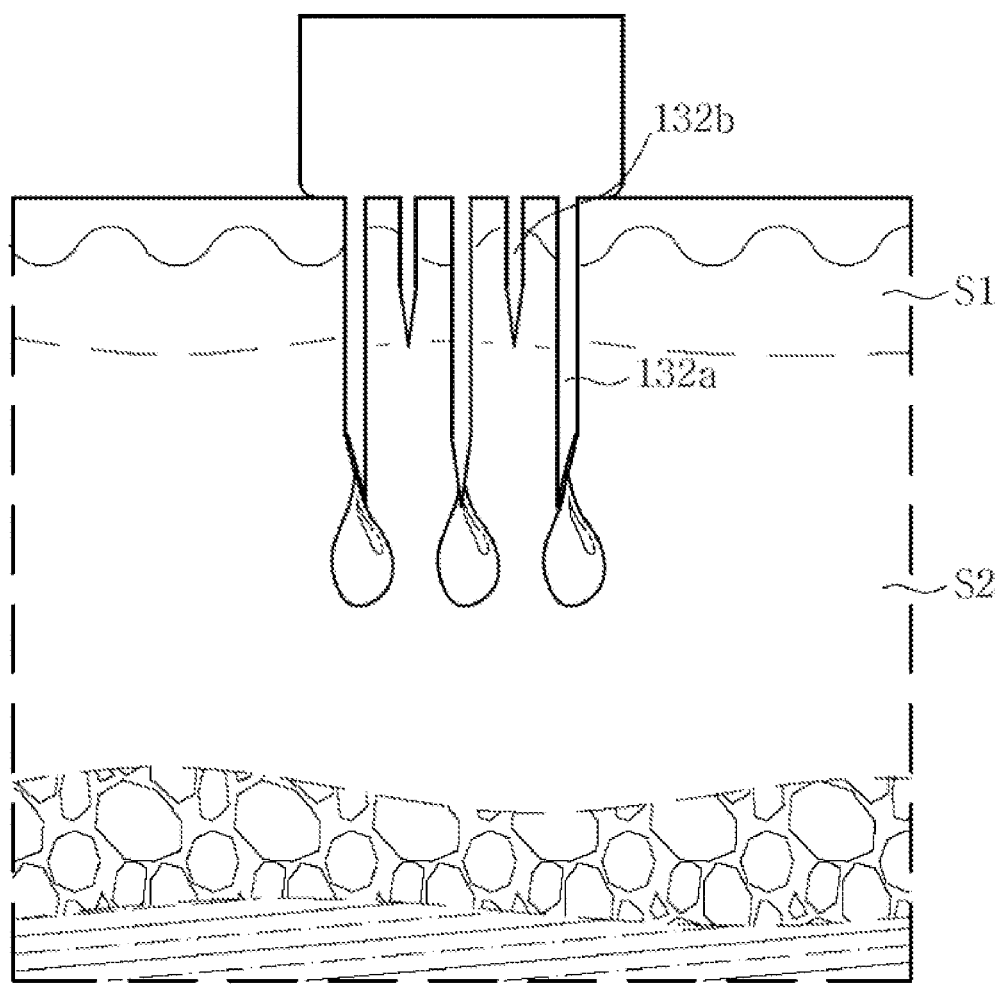

As shown in FIGS. 11 and 12, the first needles 132a are longer than the second needles 132b and configured to be inserted into a reticular hypodermis layer S2 of the skin to generate heat from a high-frequency current and inject a drug, and the second needles 132b are shorter than the first needles 132a and configured to be inserted into a papillary dermis layer S1 of the skin to generate heat from a high-frequency current. The first needles 132a may protrude downward by 1.0 mm from the needle holder 131, and the second needles 132b may protrude downward by 0.4 mm from the needle holder 131. Here, as shown in FIG. 9, a bending prevention base 132c is fitted onto an outer circumferential surface of each of the first needles 132a longer than the second needles 132b. The bending prevention base 132c supports the outside of the second needle 132b. Therefore, the first needles 132a, which are long, may be effectively suppressed from being bent due to resistance when inserted into the skin. The bending prevention base 132c is provided to be fitted onto an upper outer circumferential surface of the first needle 132a except the lower end of the first needle 132a to be inserted into the skin.

Figure 10:
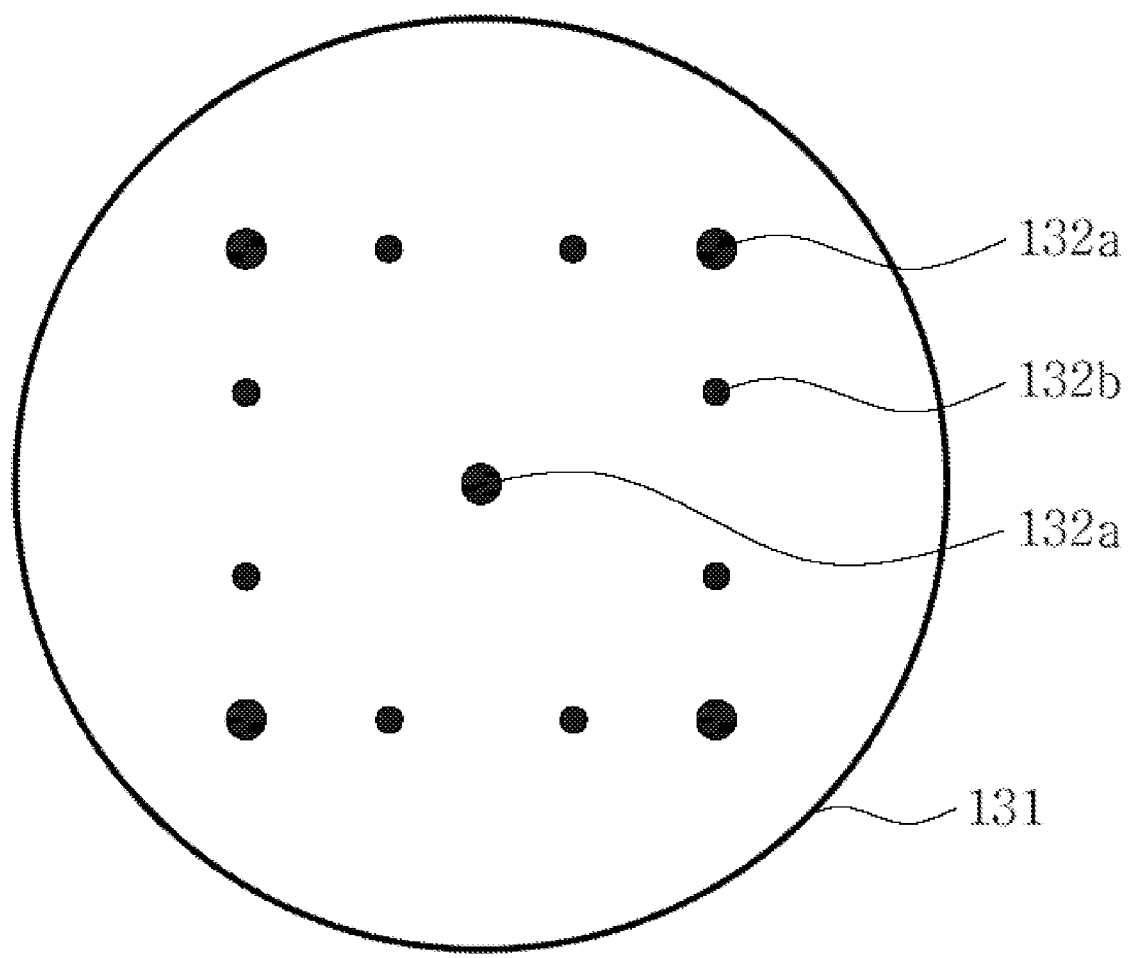
FIG. 10 is a reference diagram for describing an arrangement of a first needle and a second needle in a skin treatment device according to an embodiment of the present disclosure.

The first needles 132a are electrically connected to the high-frequency generator to generate heat from a high-frequency current and inject a drug, have inner hollow portions, and are installed to communicate with the hollow portion of the needle holder 131. The second needles 132b have a solid core body with no inner hollow portion unlike the first needles 132a and are electrically connected to the high-frequency generator. As shown in FIGS. 9 and 10, in an arrangement of the first needles 132a and the second needles 132b, one of the first needles 132a to be inserted into the reticular hypodermis layer S2 is installed at a midpoint on the needle holder 131, and the other first needles 132a are disposed around the first needle 132a at the midpoint to be spaced the same distance from each other. The second needles 132b to be inserted to the papillary dermis layer S1 are disposed between the first needles 132a disposed around the first needle 132a at the midpoint. As shown in FIG. 11, according to the above configuration, heat may be generated using a high-frequency current from both the reticular hypodermis layer S2 and the papillary dermis layer S1 but a heat density at the papillary dermis layer S1 may be increased to be higher than that at the reticular hypodermis layer S2. A density of heat from a high-frequency current may be more concentrated on epidermis than on hypodermis. A drug may be stably injected into the reticular hypodermis layer located at a deep point of the hypodermis as shown in FIG. 12.

The high-frequency generator is installed inside the handpiece main body 110 and electrically connected to both the first needles 132a and the second needles 132b so as to supply a high-frequency current to the first needles 132a and the second needles 132b, thereby generating heat.

The drug provider 140 is installed inside the handpiece main body 110 to communicate with the hollow portion of the needle holder 131 so as to supply a drug to the first needles 132a. The drug provider 140 is provided in the form of a syringe inside the handpiece main body 110 to communicate with the needle holder 131 and convey the drug to the reticular hypodermis layer S2 through the hollow portions of the first needles 132a inserted into the skin.

Figure 4:
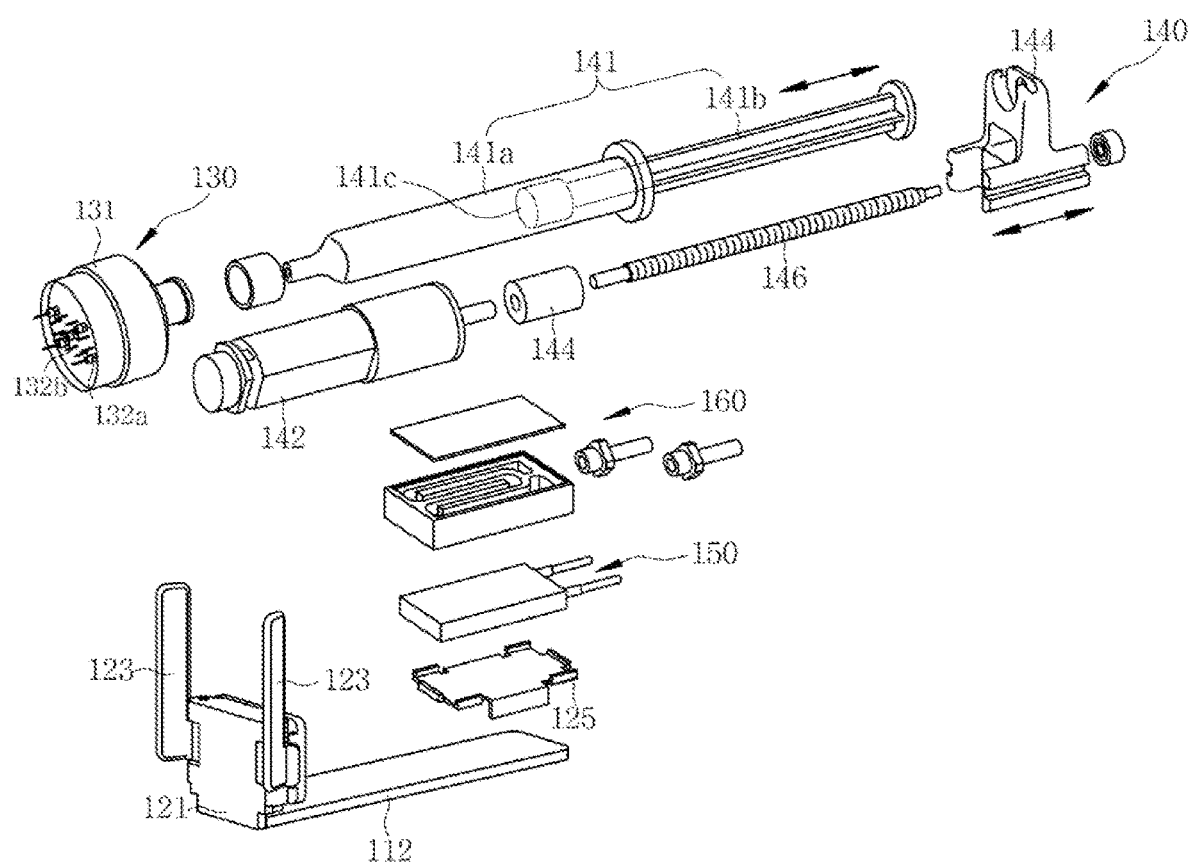
FIG. 4 is an exploded perspective view of a skin treatment device according to an embodiment of the present disclosure.
Figure 5:
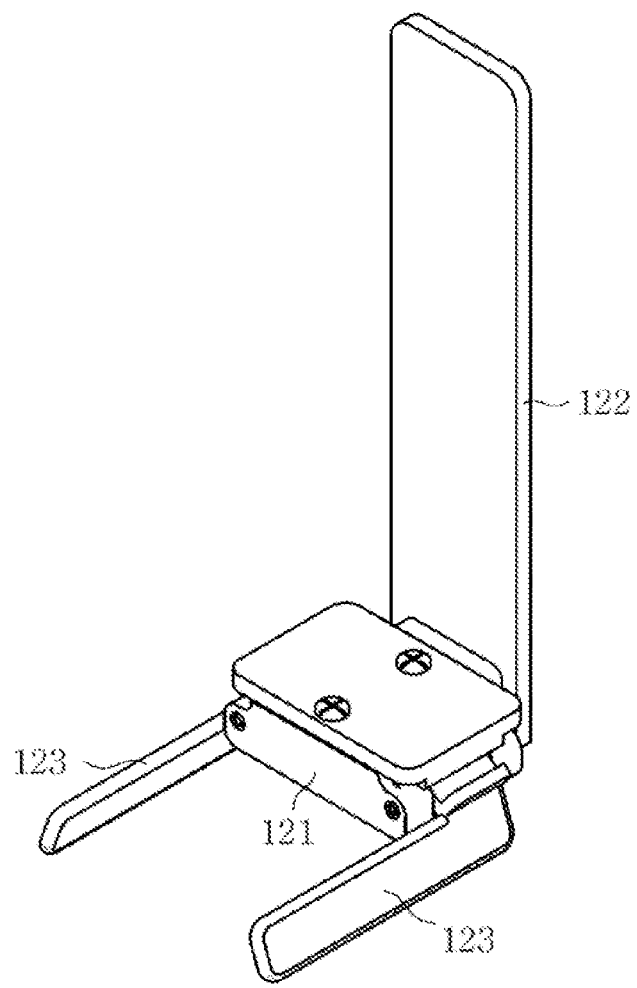
FIG. 5 is a perspective view of a skin expansion module of a skin treatment device according to an embodiment of the present disclosure.

As shown in FIG. 4, the drug provider 140 includes the syringe 141 including a cylindrical cylinder part 141a communicating with the needle holder 131, a piston part 141b installed to slide within the cylinder part 141a to pressurize a drug injected into the cylinder part 141a to be discharged to the needle holder 131, and a sealing member 141c formed of an elastic material and provided at a front end of the piston part 141b, and a syringe driving part configured to inject a drug by moving the piston part 141b of the syringe 141 forward according to a control signal supplied from a control device. In the embodiment, the syringe driving part includes a motor 142 to be operated by a control signal supplied thereto from a control device, a screw shaft 146 to be rotated by the motor 142, and a piston operation member 144 provided with a female screw hole (not shown) to be coupled spirally with a screw thread of an outer side of the screw shaft 146, installed to slide with respect to the handpiece main body 110, and moving the piston part 141b forward while sliding through rotation of the screw shaft 146.

The syringe driving part is configured to control back pressure generated during the injection of the drug. The drug contained in the cylinder part 141a of the syringe 141 is in a dosage form with a high viscosity, and the sealing member 141c at the front end of the piston part 141b is partially compressed due to the viscosity of the drug when the drug is injected by pushing the piston part 141b by the syringe driving part. Therefore, the amount of the drug discharged while the elastic member 141c formed of the elastic material such as rubber is restored to an original state after being compressed has a high discharge value at an initial stage but has a slow discharge value at a later stage. Therefore, in order to inject a desired amount of the drug, it takes a considerable time until the drug is discharged.

Accordingly, in order to quickly convey the drug, an output of the motor 142 may be controlled to be higher by about 20 to 40% (depending on the amount of the drug, e.g., 20% at a small amount of the drug and 40% at a large amount of the drug) than a target value, in consideration of the compression of the sealing member 141c so that a desired amount of the drug may be injected within a predetermined time period by increasing a moving distance of the piston operation member 144 by 20 to 40%. For example, when the volume of the drug to be injected is 100, the output of the motor 142 is controlled such that a rate of change of the internal volume of the cylinder part 141a due to the movement of the piston part 141b of the syringe 141 is in a range of 120 to 140 rather than 100.

In this case, when the motor 142 is controlled according to a value greater than a target value to move the piston part 141b forward, the sealing member 141c is compressed resulting in back pressure due to the viscosity of the drug as described above, and thus, the piston part 141b is moved backward by a certain distance to cancel compression between the back pressure and the sealing member 141c. In this case, a total distance of the backward movement is the same as a rate of increase of the forward movement described above. The backward movement of the piston part 141b is not controlled at once but is controlled step by step. For example, when the piston part 141b is moved forward by increasing a moving distance of the piston operation member 144 by 40%, compared to a target value of 100 (a moving distance corresponding to the volume of the drug), the piston part 141b is compressed and thus is not moved forward by 140 but is moved by about 80 to 90. In this case, when the motor 142 is controlled backward to move the piston part 141b backward by 20 corresponding to 50% of the total rate of increase of the moving distance, i.e., 40%, during the forward movement, the internal pressure of the syringe 141 is sharply reduced, thus causing the desired amount of the drug to be discharged. However, because the drug is gathered on a tip of a lower end of the first needle 132a or is partially discharged from the first needle 132a due to an error, the piston part 141b is additionally moved backward by 15 to cancel remaining pressure in the syringe 141 and is moved backward again by 15 to stop the discharging of the drug at an end of the needle 123. That is, 50% of a desired total degree of the backward movement of the piston part 141b is implemented when an amount of injection of the drug is substantially the same as a primary target level, secondly, 30% of the desired total degree of the backward movement is implemented to remove the internal pressure of the syringe 141, and thirdly, the remaining 20% of the desired total degree of the backward movement is implemented to stop the discharging of the drug at the end of the needle 123.

When the piston part 141b is moved backward at once after the forward movement, returning of the sealing member 141c, which is continuously compressed during the backward movement, back to the original state after the compression cannot be taken into consideration, and thus although the internal pressure of the syringe 141 is removed, air may be injected into part of the first needles 132a and the needle holder 131 after the backward movement and therefore may be injected into the skin during injection of a drug into the skin at a later time. However, as described above, when the motor 142 is controlled backward to move the piston part 141b backward, the backward movement may be controlled by being divided into at least three steps, thereby canceling back pressure and preventing the injection of the air.

The skin expansion module 120 stretches a region S of the skin into which the first needles 132a and the second needles 132b are inserted to be tightened, thereby facilitating the insertion of the first needles 132a and the second needles 132b and alleviating pain during the insertion of the first needles 132a and the second needles 132b. The skin expansion module 120 includes a guide body 121 protruding outward from the lower end of the handpiece main body 110, a heat transfer member 122 provided in contact with a cooling unit 150 installed in the handpiece main body 110 to guide a cooling source to be provided to the guide body 121, and a pair of tightening members 123 respectively hinge-coupled to hinge shafts 121d on a left side and a right side of the guide body 121 to be rotatable so that when the handpiece main body 110 is moved downward, lower ends of the pair of tightening members 123 may be spread outward in contact with the skin while pressurizing the skin.

Figure 6:
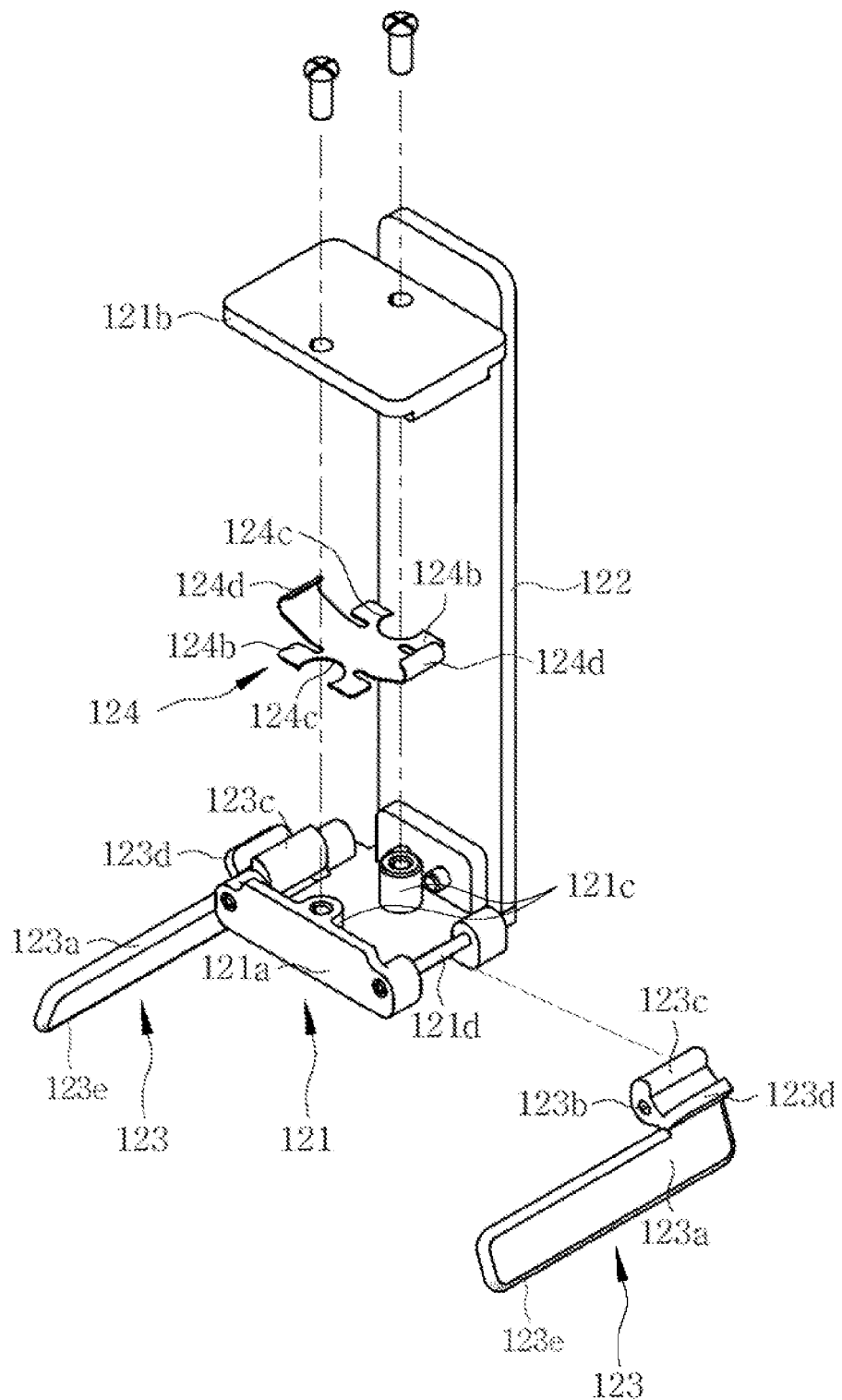
FIG. 6 is an exploded perspective view for describing a configuration of a skin expansion module of a skin treatment device according to an embodiment of the present disclosure.

As shown in FIG. 6, the tightening members 123 include skin contact parts 123a inclined to be spread outward when the lower ends of the tightening members 123 are pushed in contact with the skin, and rotational coupling parts 123b each integrally formed with an upper end of one of the skin contact parts 123a and hinge-coupled to the hinge shafts 121d on the left and right sides of the guide body 121 to be rotatable about the hinge shafts 121d. A support bump 123c protrudes upward from the upper end of the rotational coupling part 123b and is configured to be moved away from the skin contact part 123a with respect to the hinge shaft 121d installed on the guide body 121 and elastically supported more strongly by an elastic member 124 as the skin contact part 123a is spread to a larger extent.

Figure 7:
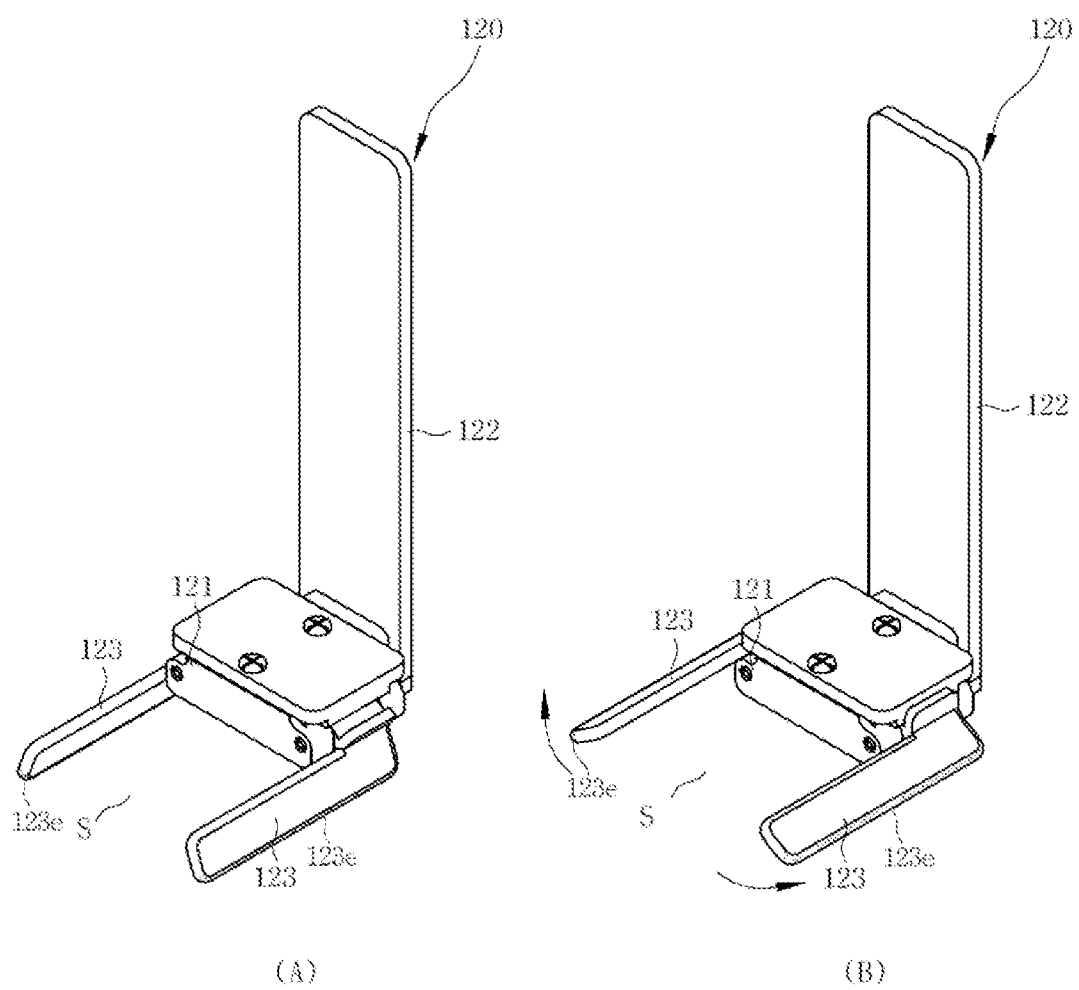
FIG. 7 is a perspective view illustrating an operation of spreading tightening members of a skin expansion module of a skin treatment device outward according to an embodiment of the present disclosure.
Figure 8:
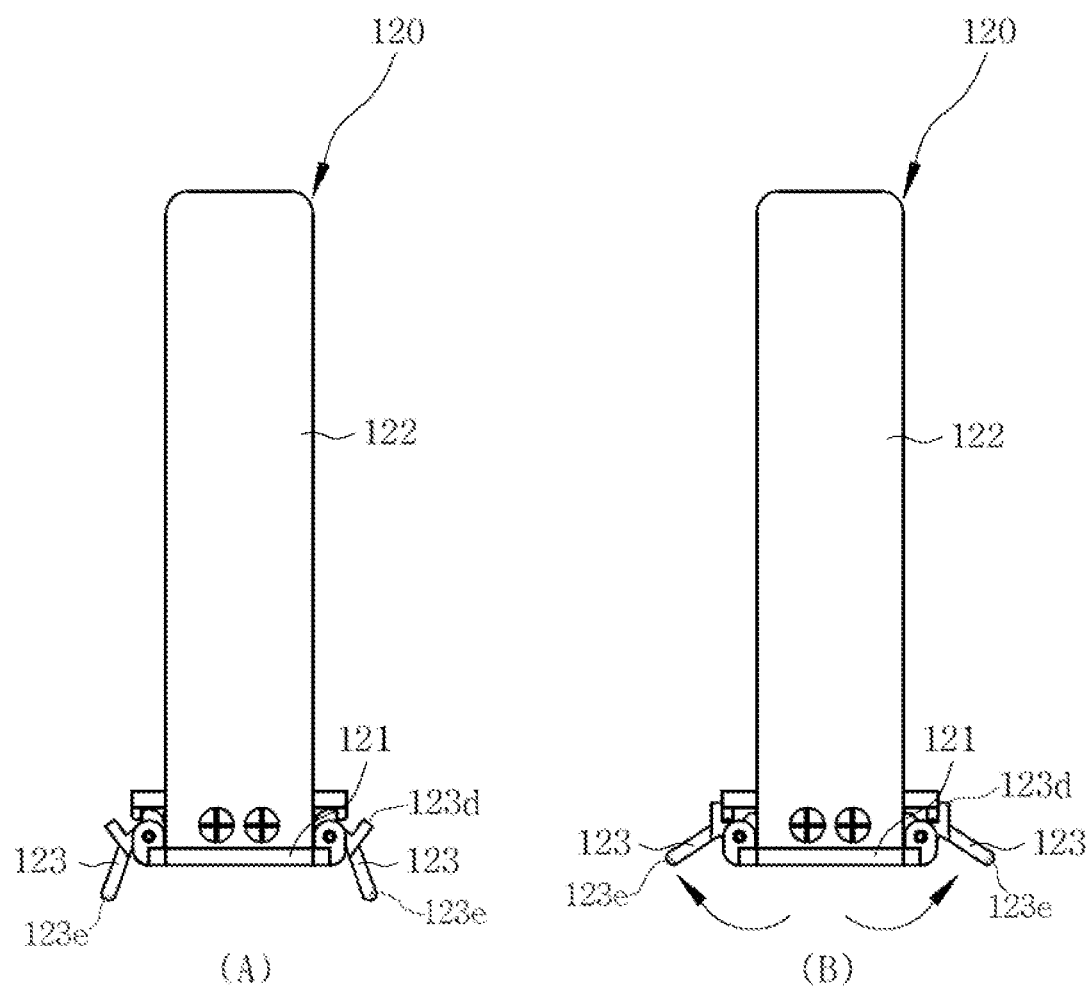
FIG. 8 is a front view illustrating an operation of spreading tightening members of a skin expansion module of a skin treatment device outward according to an embodiment of the present disclosure.

Due to the above configuration, as shown in FIGS. 7 and 8, when the first needles 132a and the second needles 132b are inserted into the skin by pressing the skin treatment device 100 according to the embodiment of the present disclosure, the tightening members 123 are rotatably spread toward left and right sides to stretch the region S of the skin into which the first and second needles 132a and 132b are to be inserted to be tightened. As the tightening members 123 are pressed more and more, the tightening members 123 tend to return to the original state more strongly. When the tightening members 123 are spread to a maximum degree, a height of a lower line of the skin contact part 123a is the same as that of a bottom surface of the guide body 121. FIGS. 7A and 8A illustrate initial states in which the pair of tightening members 123 have been yet to be spread outward, and FIGS. 7B and 8B illustrate states in which the pair of tightening members 123 are rotated to be fully spread outward. FIG. 8B illustrates that when the pair of tightening members 123 are spread to the maximum degree, the height of the lower line of the skin contact part 123a is the same as that of the bottom surface of the guide body 121.

An upper end of the rotational coupling part 123b of the tightening member 123 is further provided with a stopper bump 123d protruding from a point spaced outward from the support bump 123c. The stopper bump 123d is caught by an outer side of the guide body 121 to block the rotation of a pair of skin contact parts 123a not to spread when the pair of skin contact parts 123a are spread to a maximum degree. Therefore, a force causing the skin to be stretched and tightened may be prevented from weakening. A non-slip member 123e formed of a rubber material having a higher coefficient of friction than that of the skin contact part 123a may be attached to the lower line of the skin contact part 123a of the tightening member 123 and an inner side thereof adjacent to the lower line. Therefore, a slip phenomenon that may occur when the skin contact parts 123a of the tightening members 123 are spread outward in contact with the skin may be minimized.

In the skin expansion module 120, the guide body 121 is provided as a flat tetragonal box-shaped member. The guide body 121 has a space in which the elastic member 124 is installed, and is formed by combining a lower body 121a with hinge shafts 121d at left and right sides thereof and an upper cover 121b to be combined with an upper portion of the lower body 121a. A lower side of the guide body 121 is provided as a flat surface to enhance the adhesion to the skin and increase an area to be cooled. The guide body 121 is connected to the heat transfer member 122 in contact with a cooling unit 150 to supply a cooling source provided from the cooling unit 150 to the skin, thereby cooling the skin.

The heat transfer member 122 of the skin expansion module 120 is formed of a thermally conductive metal material, together with the guide body 121, and disposed in contact with the cooling unit 150 installed in the handpiece main body 110 through a heat transfer gasket 125, and a lower end thereof is coupled to a rear end of the guide body 121. The heat transfer member 122 transfers the cooling source provided from the cooling unit 150 to the guide body 121 in direct contact with the skin. Here, the cooling unit 150 is provided as a thermoelement, and the guide body 121 is disposed in contact with a cooling part of the thermoelement while the heat transfer gasket 125 is interposed therebetween. In this case, a heat dissipation module 160 is installed adjacent to a heat generation part of the thermoelement.

The elastic member 124 is configured to maintain the pair of tightening members 123 to be inclined at a certain angle in an initial state in which an external force is not applied and more strongly and elastically support the pair of tightening members 123 as the pair of tightening members 123 in contact with the skin moves away from the skin. To this end, the elastic member 124 is provided as a circular arc shaped leaf spring gradually curved upward toward left and right ends from a central portion supported on an inner bottom surface of the guide body 121 so that the support bumps 123c of the tightening members 123 may be elastically supported by the left and right ends. The left and right ends of the elastic member 124 are provided with inwardly curved contact parts 124d to be in continuous contact with the support bumps 123c regardless of an angle of rotation of the tightening members 123. A fixing part 124b having a semicircular groove 124c to be fixed by being fitted onto an outer circumferential surface of a cylindrical spacer of the guide body 121 is further formed in front of and behind the central portion of the elastic member 124. Due to the fixing part 124b, the elastic member 124 may stably support the tightening members 123 without leaning to a left or right side.

It is noted that the elastic member 124 is configured as a leaf spring rather than a coil spring or a torsion spring to secure more stable and elastic bearing power with respect to the tightening members 123. In order to provide the elastic member 124 in the form of a large leaf spring, the left and right sides of the guide body 121 are opened while the elastic member 124 is seated in the guide body 121, and the contact parts 124d on the left and right ends of the elastic member 124 may elastically support the support bumps 123c of the tightening members 123 in contact with the support bumps 123c through the opened left and right sides of the guide body 121. In addition, the hinge shafts 121d are provided on the opened left and right sides of the guide body 121 so that the tightening members 123 are elastically supported in continuous contact with the contact part 124d of the elastic member 124 while being hinge-coupled to be rotatable.

A skin treatment device according to the present disclosure is capable of improving a treatment effect by generating heat from a high-frequency current and injecting a drug in parallel and stretching the skin to be tightened through a pair of tightening members during insertion of needles so that the insertion of the needles, the generation of heat, and the injection of the drug can be smoothly implemented.

According to the present disclosure, due to an arrangement of first needles configured to be inserted into the reticular hypodermis layer of the skin to generate heat from a high-frequency current and inject a drug and second needles configured to be inserted into the papillary dermis layer of the skin to generate heat from a high-frequency current, a density of heat generated from a high-frequency current at the papillary dermis layer closer to epidermis of the skin can be increased as compared to that of the reticular hypodermis layer, and a drug can be stably injected into the reticular hypodermis layer located deeply in the skin. Furthermore, because the first and second needles are inserted into the skin while the skin is stretched to be tightened by tightening members, a depth of insertion of the first and second needles can be controlled consistently and exactly.

Although example embodiments of the present disclosure have been described above, the present disclosure should be understood to cover various modifications, equivalents, and alternatives falling within the scope of the present disclosure. It will be apparent that the above embodiments are applicable to the present disclosure through simple modifications thereto. Therefore, the foregoing description should not be construed as limiting the scope of the present disclosure defined by the following claims.

What is claimed is:

1. A skin treatment device using both high frequencies and medication, comprising:
   a handpiece main body;
   a needle module including a needle holder installed outside a lower end of the handpiece main body and including a hollow portion, and multiple first needles protruding downward from a lower end of the needle holder, including a hollow portion communicating with the hollow portion of the needle holder, and configured to be inserted into the skin;
   a high-frequency generator provided in the handpiece main body and electrically connected to the first needles to supply a high-frequency current to the first needles so as to generate heat;
   a drug provider provided in the handpiece main body to communicate with the hollow portion of the needle holder and configured to provide a drug to the first needles; and
   a skin expansion module configured to stretch a region of the skin into which lower ends of the first needles are inserted to be tightened, the skin expansion module including a guide body protruding outward from the lower end of the handpiece main body, and a pair of tightening members hinge-coupled to hinge shafts provided on a left side and a right side of the guide body to be rotatable, wherein lower ends of the pair of tightening members are spread outward while pressurizing the skin in contact with the skin when the handpiece main body is moved downward,
   wherein an elastic member is provided in the guide body to elastically support the tightening members and maintain the tightening members to be inclined at a certain angle in an initial state in which an external force is not applied, and
   the pair of tightening members tend to be more strongly and elastically supported by the elastic member as the pair of tightening members become spread while in contact with the skin.

2. The skin treatment device of claim 1, wherein the tightening members each comprise:
   a skin contact part inclined to be spread outward when a lower end thereof is pressed while in contact with the skin; and
   a rotational coupling part integrally formed with an upper end of the skin contact part and hinge-coupled to the hinge shafts provided on the left and right sides of the guide body to be rotatable about the hinge shafts,
   wherein support bumps protrude upward from an upper end of the rotational coupling part to be moved away from the skin contact part with respect to the hinge shafts and are more strongly and elastically supported on the elastic member as the skin contact parts are spread outward.

3. The skin treatment device of claim 2, further comprising a stopper bump protruding from a position on an upper end of the rotational coupling part of the tightening member, which is spaced outward from the support bump, the stopper bump being configured to be caught by an outer side of the guide body to block further rotation of the skin contact part when lower lines of the pair of skin contact parts are at the same height as a bottom side of the guide body.

4. The skin treatment device of claim 3, wherein a fixing part having a semicircular groove to be fixed by being fitted onto an outer circumferential surface of a cylindrical spacer of the guide body is further formed in front of and behind a central portion of the elastic member.

5. The skin treatment device of claim 2, wherein the elastic member is provided as a circular arc shaped leaf spring gradually curved upward toward left and right ends from a central portion supported on an inner bottom surface of the guide body to elastically support the support bumps of the tightening members by the left and right ends of the elastic member, and
   the left and right ends of the elastic member are further provided with inwardly curved contact parts corresponding to the support bumps to be in continuous contact with the support bumps regardless of an angle of rotation of the tightening members.

6. The skin treatment device of claim 2, wherein a non-slip member having a strip shape and having a higher coefficient of friction than that of the skin contact part is further attached to a lower line of the skin contact part of each tightening member.

7. The skin treatment device of claim 1, wherein the skin expansion module is formed of a thermally conductive metal material and further comprises a heat transfer member in contact with a cooling unit installed in the handpiece main body to supply a cooling source to the guide body.

8. The skin treatment device of claim 7, wherein a lower side of the guide body is provided as a flat surface to increase an area of the skin to be cooled.

9. The skin treatment device of claim 7, wherein the cooling unit comprises a thermoelement disposed in contact with the heat transfer member and configured to supply a cooling source.

10. The skin treatment device of claim 1, wherein the needle module further comprises multiple second needles protruding downward from the lower end of the needle holder and electrically connected to the high-frequency generator to be supplied with a high-frequency current and generate heat, and
    the first needles are configured to inject a drug in a state in which lower ends thereof reach a reticular hypodermis layer when the first needles are inserted into the skin, and to be supplied with a high-frequency current and generate heat, and the second needles are shorter than the first needles and configured to be supplied with a high-frequency current and generate heat when lower ends thereof reach a papillary dermis layer when the second needles are inserted into the skin.

11. The first needles configured to be inserted into the reticular hypodermis layer include a midpoint needle disposed at a midpoint on the needle holder and a plurality of vicinity needles disposed in the vicinity of the midpoint to be spaced apart from each other, and the second needles configured to be inserted to the papillary dermis layer are disposed between the vicinity needles around the midpoint needle to increase a density of heat from the high-frequency current to be higher than a density of heat at the reticular hypodermis layer.

12. The skin treatment device of claim 10, wherein a bending prevention base is fitted onto an outer circumferential surface of each of the first needles longer than the second needles.

13. The skin treatment device of claim 10, wherein the first needles protrude downward by 1.0 mm from the needle holder, and the second needles protrude downward by 0.4 mm from the needle holder.

* * * * *